United States Patent
Mishra et al.

[11] Patent Number: 6,011,034
[45] Date of Patent: Jan. 4, 2000

[54] INSECTICIDAL DIHYDROOXADIAZINE COMPOUNDS

[75] Inventors: Anupama Mishra, Guelph; Mark Achiel Dekeyser, Waterloo, both of Canada; Paul Thomas McDonald, Middlebury, Conn.

[73] Assignees: Uniroyal Chemical Company, Inc., Middlebury, Conn.; Uniroyal Chemical Co./CIE., Elmira, Canada

[21] Appl. No.: 09/022,616

[22] Filed: Feb. 12, 1998

[51] Int. Cl.⁷ .................. A01N 43/707; A01N 43/88; C07D 273/04; C07D 285/18

[52] U.S. Cl. .................... 514/229.2; 514/222.5; 514/222.8; 514/242; 514/243; 544/8; 544/10; 544/11; 544/66; 544/68; 544/182; 544/183

[58] Field of Search .................... 544/8, 66, 68, 544/182; 514/222.5, 229.2, 242

[56] References Cited

U.S. PATENT DOCUMENTS

| | | | |
|---|---|---|---|
| 3,420,825 | 1/1969 | Trepanier | 260/244 |
| 3,420,826 | 1/1969 | Trepanier | 260/244 |
| 5,462,938 | 10/1995 | Annus | 514/229.8 |
| 5,536,720 | 7/1996 | Dekeyser | 514/229.2 |

OTHER PUBLICATIONS

Trepanier et al, "5,6–Dihydro–4H–1,3,4–Oxadiazines. V. Base–Catalyzed Cyclodehydrohalogenation of 2–(β–Chloroalkyl)carboxylic Acid Hydrazides", J. Med. Chem. 9: 753–758 (1966).

Primary Examiner—Richard L. Raymond
Attorney, Agent, or Firm—Daniel Reitenbach

[57] ABSTRACT

Insecticidal dihydrooxadiazine compounds having the formula:

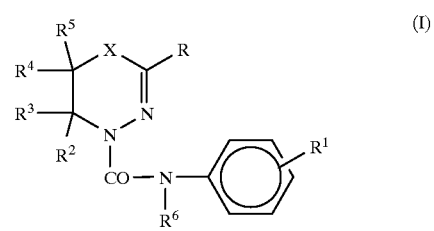

wherein X is O or S; R is a substituted or unsubstituted phenyl or heterocyclic group; $R^1$ is halogen, haloalkyl or haloalkoxy; $R^2$, $R^3$, and $R^4$ are, independently, hydrogen, alkyl or alkoxy; $R^5$ is nitro, cyano, alkoxy, alkyl, haloalkoxy, dialkylamino, alkylthio, phenoxy, phenylthio, or alkoxycarbonyl; $R^6$ is hydrogen, alkyl, alkylthio, alkoxyalkyl, alkoxycarbonyl, acyl, or benzyl, wherein $R^3$ and $R^5$ together can form a ring.

15 Claims, No Drawings

INSECTICIDAL DIHYDROOXADIAZINE COMPOUNDS

FIELD OF THE INVENTION

This invention relates to insecticidal substituted dihydrooxadiazine compounds, insecticidal compositions containing the dihydrooxadiazine compounds, and methods for their use.

BACKGROUND OF THE INVENTION

Certain oxadiazine compounds have been described as useful as pesticides and as pharmaceutical agents. For example, U.S. Pat. No. 5,536,720 describes substituted 2-phenyl-1,3,4-oxadiazine-4-carbamide compounds useful as insecticides and acaricides. Trepanier et al, J. Med. Chem 9: 753–758 (1966) describe certain 2-substituted 4H-1,3,4-oxadiazines useful as anticonvulsants in mice. U.S. Pat. No. 3,420,826 describes certain 2,4,6-substituted 4H-1,3,4-oxadiazines, useful as sedatives, anticonvulsants, and as pesticides against nematodes, plants, and fungi. U.S. Pat. No. 3,420,825 describes methods for producing certain 2,4,6-substituted 4H-1,3,4-oxadiazines.

It is a purpose of this invention to provide novel dihydrooxadiazine derivatives useful as insecticides.

SUMMARY OF THE INVENTION

The present invention relates to a compound having the formula:

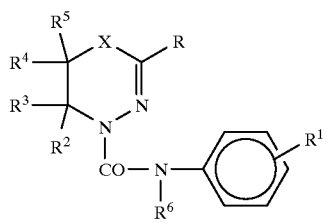

(I)

wherein X is O or S; R is phenyl, a $C_4$–$C_5$ heterocyclic group containing one nitrogen, sulfur, or oxygen atom, wherein the phenyl or heterocyclic group is unsubstituted or mono-, di-, or tri-substituted with halogen, $C_1$–$C_4$ haloalkyl; or $C_1$–$C_4$ haloalkoxy; $R^1$ is halogen, $C_1$–$C_4$ haloalkyl or $C_1$–$C_4$ haloalkoxy; $R^2$, $R^3$, and $R^4$ are, independently, hydrogen, $C_1$–$C_6$ alkyl or $C_1$–$C_6$ alkoxy; $R^5$ is nitro, cyano, $C_1$–$C_6$ alkyl, di($C_1$–$C_6$)alkylamino, $C_1$–$C_6$ alkylthio, $C_1$–$C_6$ alkoxy, $C_1$–$C_6$ haloalkoxy, phenoxy, phenylthio, or ($C_1$–$C_6$ alkoxy) carbonyl; $R^6$ is hydrogen, $C_1$–$C_6$ alkyl, $C_1$–$C_4$ alkylthio, ($C_1$–$C_4$ alkoxy)$C_1$–$C_4$ alkyl, $C_2$–$C_8$ acyl, ($C_1$–$C_6$ alkoxy) carbonyl, or benzyl, wherein $R^3$ and $R^5$ together can form a ring. These compounds, or physiologically acceptable salts thereof, are useful as insecticides.

The insecticidal compositions of this invention comprise: (a) an effective amount of one or more compounds of formula I, and (b) a suitable carrier.

DETAILED DESCRIPTION OF THE INVENTION

Preferably, the compound of this invention has the formula:

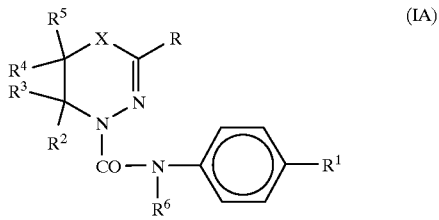

(IA)

wherein R, $R^1$, $R^2$, $R^3$, $R^4$, $R^5$, $R^6$, and X are as described

R is preferably phenyl, thienyl, furanyl, pyridinyl, optionally mono-, di- or tri-substituted by bromo, chloro, trihaloalkyl, or trihaloalkoxy, more preferably, one bromo, one chloro, one trihalomethyl, one trihaloethyl, one trihalomethoxy, or one trihaloethoxy. Particularly preferred is the compound of formula IA wherein R is phenyl, thienyl, or pyridinyl, substituted by bromo, chloro, methyl, trifluoromethyl, or trifluoromethoxy.

Preferably, X is O; $R^1$ is $C_1$–$C_4$ trihaloalkyl or $C_1$–$C_4$ trihaloalkoxy, more preferably, trihalomethyl or trihalomethoxy; $R^2$, $R^3$, and $R^4$ are, independently, $C_1$–$C_4$ alkyl or $C_1$–$C_4$ alkoxy, more preferably, methyl, ethyl, methoxy, or ethoxy; $R^5$ is $C_1$–$C_4$ alkoxy, $C_1$–$C_4$alkyl, $C_1$–$C_4$ alkylthio, or di($C_1$–$C_4$)alkylamino, more preferably, methoxy or ethoxy; and $R^6$ is hydrogen, $C_1$–$C_4$ alkyl, $C_1$–$C_4$ alkylthio, ($C_1$–$C_4$ alkoxy)methyl or $C_2$–$C_8$ acyl, more preferably, methyl, methylthio, methoxymethyl or acetyl.

The compounds and compositions of this invention are useful as plant protecting agents against insects and are particularly effective against coleopterous insects and lepidopterous insects, such as tobacco budworm.

The compounds of the instant invention can be prepared by reacting an oxadiazine of formula A below, wherein R, $R^2$, $R^3$, $R^4$, $R^5$, and X are as described above, with an isocyanate of formula B below, wherein $R^1$ is as described above, and a catalytic amount of triethylamine in a suitable solvent such as acetonitrile or toluene, to produce the compound of formula IB (the compounds of formula I in which $R^6$ is hydrogen).

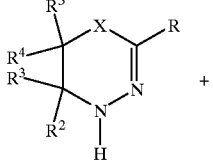

(A)

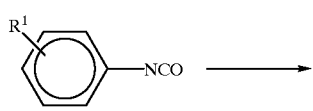

(B)

-continued

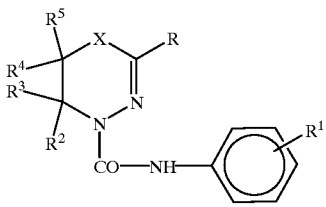

(IB)

The compounds of formula I in which $R^6$ is $C_1$–$C_6$ alkyl, $C_1$–$C_4$ alkylthio, ($C_1$–$C_4$ alkoxy)$C_1$–$C_4$ alkyl, $C_2$–$C_8$ acyl, or benzyl, can be prepared by reacting the compound of formula IB with $R^6Y$ wherein Y is halogen and $R^6$ is $C_1$–$C_6$ alkyl, $C_1$–$C_4$ alkylthio, ($C_1$–$C_4$ alkoxy)$C_1$–$C_4$ alkyl, $C_2$–$C_8$ acyl, or benzyl, with a suitable base such as triethylamine or sodium hydride.

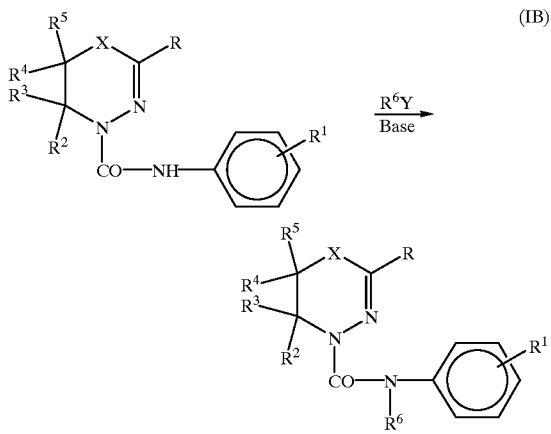

($R^6$ = alkyl, alkylthio, alkoxyalkyl, acyl, or benzyl)

Compounds of formula A above can be prepared by the cyclization of an azo compound (RCXN=NCO$_2$C$_2$H$_5$) with an alkene of the formula:

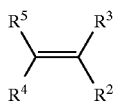

wherein R, $R^2$, $R^3$, $R^4$, $R^5$, and X are as described above, followed by hydrolysis of the resultant intermediate.

The compositions of the present invention can be prepared by formulating one or more compounds of the present invention with a suitable carrier.

Suitable liquid carriers can comprise water, alcohols, ketones, phenols, toluene and xylenes. In such formulations, additives conventionally employed in the art can be utilized, such as one or more surface active agents and/or inert diluents, to facilitate handling and application of the resulting insecticidal composition.

Alternatively, the compounds of this invention can be applied as a liquid or in sprays when utilized in a liquid carrier, such as a solution comprising a compatible solvent such as acetone, benzene, toluene or kerosene, or a dispersion comprising a suitable non-solvent medium such as water.

The compositions of this invention can alternatively comprise solid carriers taking the form of dusts, granules, wettable powders, pastes, aerosols, emulsions, emulsifiable concentrates, and water-soluble solids. For example, the compounds of this invention can be applied as dusts when admixed with or absorbed onto powdered solid carriers, such as mineral silicates, talc, pyrophyllite and clays, together with a surface-active dispersing agent so that a wettable powder is obtained which then is applied directly to the loci to be treated. Alternatively, the powdered solid carrier containing the compound admixed therewith, can be dispersed in water to form a suspension for application in such form.

Granular formulations of the compounds are preferred for field treatment and are suitable for application by broadcasting, side dressing, soil incorporation or seed treatment, and are suitably prepared using a granular or pelletized form of carrier such as granular clays, vermiculite, charcoal or corn cobs. The compound of this invention is dissolved in a solvent and sprayed onto an inert mineral carrier such as attapulgite granules (10–100 mesh), and the solvent is then evaporated. Such granular compositions can contain from 2–25% of a compound of this invention, based on carrier plus compound, preferably, 3–15%. In addition, the compounds of this invention can also be incorporated into a polymeric carrier such as polyethylene, polypropylene, butadiene-styrene, styrene-acrylonitrile resins, polyamides, poly(vinyl acetates), and the like. When encapsulated, the compound of this invention can advantageously be released over an even longer time period, extending its effectiveness further than when used in non-encapsulated form.

Another method of applying the compound of this invention to the loci to be treated is by aerosol treatment, for which the compound can be dissolved in an aerosol carrier which is a liquid under pressure but which is a gas at ordinary temperature (e.g., 20° C.) and atmospheric pressure. Aerosol formulations can also be prepared by first dissolving the compound in a less volatile solvent and then admixing the resulting solution with a highly volatile liquid aerosol carrier.

For treatment of plants (such term including plant parts), the compounds of the invention preferably are applied in aqueous emulsions containing a surface-active dispersing agent which can be non-ionic, cationic or anionic. Suitable surface-active agents are well known in the art, such as those disclosed in U.S. Pat. No. 2,547,724 (columns 3 and 4). The compounds of this invention can be mixed with such surface-active dispersing agents, with or without an organic solvent, as concentrates for the subsequent addition of water, to yield aqueous suspensions of the compounds at desired concentration levels.

In addition, the compounds can be employed with carriers which themselves are pesticidally active, such as insecticides, acaricides, fungicides or bactericides.

It will be understood that the effective amount of a compound in a given formulation will vary depending, e.g., upon the specific pest to be combated, as well as upon the specific chemical composition and formulation of the compound being employed, the method of applying the compound/formulation and the locus of treatment. Generally, however, the effective amount of the compound of this invention can range from about 0.1 to about 95 percent by weight. Spray dilutions can be as low as a few parts per million, while at the opposite extreme, full strength concentrates of the compound can be usefully applied by ultra low volume techniques. When plants constitute the loci of treatment, concentration per unit area can range between about 0.01 and about 50 pounds per acre, with concentrations of between about 0.1 and about 10 pounds per acre preferably being employed for crops such as corn, tobacco, rice and the like.

To combat insects, sprays of the compounds can be applied to any suitable locus, such as to the insects directly and/or to plants upon which they feed or nest. The compositions of this invention can also be applied to the soil or other medium in which the pests are present.

The specific methods of application of the compounds and compositions of this invention, as well as the selection and concentration of these compounds, will vary depending upon such circumstances as crops to be protected, geographic area, climate, topography, plant tolerance, etc.

The following examples are provided to illustrate the present invention.

EXAMPLES

Example 1

Preparation of 6-ethoxy-5,6-dihydro-N-[4-(trifluoromethoxy)phenyl]-2-[3-(trifluoromethyl) phenyl]-4H-1,3,4-oxadiazine-4-carboxamide (Compound No. 1)

A. Preparation of 2-[3-(trifluoromethyl)benzoyl]-hydrazinecarboxylic acid ethyl ester 70 g of (3-trifluoromethyl)benzoic acid hydrazide (0.34 mol) and 40 ml of pyridine were dissolved in 150 ml of N,N-dimethylformamide and stirred at 15° C. (water bath). 40 ml of ethyl chloroformate (0.41 mol) was added dropwise to this mixture while the reaction temperature was kept below 20° C. After addition of the ethylchloroformate, the resultant reaction mixture was stirred at room temperature for four hours and then 500 ml of water was added with stirring. The resultant precipitate was filtered by suction, washed with water four times, and then dried in air, to produce 80 g of 2-[3-(trifluoromethyl)benzoyl] hydrazinecarboxylic acid ethyl ester (85% yield). The structure was confirmed by infrared (IR) and nuclear magnetic resonance (NMR) spectra.

B. Preparation of 4-[3-trifluoromethyl)benzoyl]-diazenecarboxylic acid ethyl ester 15 g of 2-[3-(trifluoromethyl)benzoyl] hydrazinecarboxylic acid ethyl ester was stirred with 200 ml of dichloromethane at room temperature. 150 ml of 5% NaOCl (0.10 mol) solution was then rapidly added to the reaction mixture, which exothermed to 30° C., and stirred for three hours until all the white solid disappeared and a deep red colored organic layer appeared. This organic layer was separated, dried ($MgSO_4$), and the solvent removed to give 13.5 g of 4-[3-trifluoromethyl)benzoyl]-diazenecarboxylic acid ethyl ester (89%). The structure was confirmed by IR and NMR spectra.

C. Preparation of 6-ethoxy-5,6-dihydro-2-[3-(trifluoromethyl)phenyl]-4H-1,3,4-oxadiazine-4-carboxylic acid ethyl ester 20 g of benzene was added to 13.5 g of 4-[3-trifluoromethyl)benzoyl]-diazenecarboxylic acid ethyl ester, followed by the addition of 7 g of ethyl vinyl ether to prepare a reaction mixture. The reaction mixture was kept at room temperature overnight. After the red color of the reaction mixture faded, the solvent was removed, giving 17 g of crude 6-ethoxy-5,6-dihydro-2-[3-(trifluoromethyl)phenyl]-4H-1,3,4-oxadiazine-4-carboxylic acid ethyl ester, which was not purified and was used in Step D below.

D. Preparation of 6-ethoxy-5,6-dihydro-2-[3-(trifluoromethyl)phenyl]-4H-1,3,4-oxadiazine The crude 6-ethoxy-5,6-dihydro-2-[3-(trifluoromethyl) phenyl]-4H-1,3,4-oxadiazine-4-carboxylic acid ethyl ester (17 g) from Step C above, was mixed with 12 g of KOH, 20 g of ethanol, and 40 g of water to create a reaction mixture. The reaction mixture was refluxed for 6 hours and then cooled. 50 ml of water was then added to the reaction mixture, followed by extraction with ethyl acetate (4×100 ml). The ethyl acetate extracts were conbined, dried ($MgSO_4$) and the solvent removed, to give 7 g of crude 6-ethoxy-5,6-dihydro-2-[3-(trifluoromethyl)phenyl]-4H-1,3,4-oxadiazine, which was not purified and was used in Step E below.

E. Preparation of 6-ethoxy-5,6-dihydro-N-[4-(trifluoromethoxy)phenyl]-2-[3-trifluoromethyl) phenyl]-4H-1,3,4-oxadiazine-4-carboxamide (Compound No. 1)

The crude 6-ethoxy-5,6-dihydro-2-[3-(trifluoromethyl) phenyl]-4H-1,3,4-oxadiazine (7 g) from Step D above, was dissolved in 20 g of acetonitrile and then 5 g of (4-trifluoromethoxy)phenyl isocyanate was added, to create a reaction mixture. The reaction mixture was refluxed for four hours and then the acetonitrile was removed. The residue was then purified by column chromatography on 100 g of silica gel using 1000 ml of toluene. The toluene was removed and the residue was crystallized with methanol to give two crops of crystals, total weight 5 g (0.015 mol) of 6-ethoxy-5,6-dihydro-N-[4-(trifluoromethoxy)phenyl]-2-[3-trifluoromethyl)phenyl]-4H-1,3,4-oxadiazine-4-carboxamide (26% yield based on hydrazinecarboxylic acid ethyl ester), m.p. 105–107° C.

Example 2

Preparation of 6-ethoxy-5,6-dihydro-N-[4-(trifluoromethoxy)phenyl]-2-(4-bromophenyl)-4H-1,3,4-oxadiazine-4-carboxamide (Compound No. 2)

Prepared as described above in Example 1 except that 4-bromobenzoic acid hydrazide was used instead of 3-trifluoromethyl benzoic acid hydrazide in Step A.

Example 3

Preparation of 6-ethoxy-5,6-dihydro-N-[4-(trifluoromethoxy)phenyl]-2-(5-bromo-2-thiophenyl)-4H-1,3,4-oxadiazine-4-carboxamide (Compound No. 3)

Prepared as described above in Example 1 except that 5-bromo-2-thiophenecarboxylic acid hydrazide was used instead of 3-trifluoromethyl benzoic acid hydrazide in Step A.

Example 4

Preparation of 6-methoxy-6-methyl-5-hydro-N-[4-(trifluoromethoxy)phenyl]-2-(5-bromo-2-thiophenyl)-4H-1,3,4-oxadiazine-4-carboxamide (Compound No. 4)

Prepared as described above in Example 1 except that 5-bromo-2-thiophenecarboxylic acid hydrazide was used instead of 3-trifluoromethyl benzoic acid hydrazide in Step A and 2-methoxypropene was used instead of ethyl vinyl ether in Step C.

Example 5

Preparation of 5-methyl-6-ethoxy-5,6-dihydro-N-[4-(trifluoromethoxy)phenyl]-2-[3-(trifluoromethyl) phenyl]-4H-1,3,4-oxadiazine-4-carboxamide (Compound No. 5)

Prepared as described above in Example 1 except that ethyl-1-propenyl ether was used instead of ethyl vinyl ether in Step C.

Example 6

Preparation of (2,3-dihydrofuranyl)-N-[4-(trifluoromethoxy)phenyl]-2-(4-bromophenyl)-4H-1,3,4-oxadiazine-4-carboxamide (Compound No. 6)

Prepared as described above in Example 1 except that 4-bromobenzoic acid hydrazide was used instead of 3-trifluoromethyl benzoic acid hydrazide in Step A and 2,3-dihydrofuran was used instead of ethyl vinyl ether in Step C.

Example 7

Preparation of (3,4-dihydropyranyl)-N-[4-(trifluoromethoxy)phenyl]-2-(4-bromophenyl)-4H-1,3,4-oxadiazine-4-carboxamide (Compound No. 7)

Prepared as described above in Example 1 except that 4-bromobenzoic acid hydrazide was used instead of 3-trifluoromethyl benzoic acid hydrazide in Step A and 3,4-dihydropyran was used instead of ethyl vinyl ether in Step C.

Example 8

Preparation of 6-methoxy-5,6-dihydro-N-[4-(trifluoromethoxy)phenyl]-2-[3-(trifluoromethyl)phenyl]-4H-1,3,4-oxadiazine-4-carboxamide (Compound No. 8)

Prepared as described above in Example 1 except that methyl vinyl ether was used instead of ethyl vinyl ether in Step C.

Example 9

Preparation of 6-ethoxy-5,6-dihydro-N-[4-(trifluoromethyl)phenyl]-2-[3-(trifluoromethyl)phenyl]-4H-1,3,4-oxadiazine-4-carboxamide (Compound No. 9)

Prepared as described above in Example 1 except that (4-trifluoromethyl)phenyl isocyanate was used instead of (4-trifluoromethoxy)phenyl isocyanate in Step E.

Example 10

Preparation of 5,6-dihydro-6-methyl-N-[4-(trifluoromethyl)phenyl]-2-[4-(trifluoromethoxy)phenyl]-4H-1,3,4-oxadiazine-4-carboxamide (Compound No. 10)

A. Preparation of 2-(2-chloro-1-oxopropyl)hydrazide of 4-(trifluoromethoxy)benzoic acid 11 g of 4-(trifluoromethoxy)benzoic acid hydrazide (0.05 mol) and 6.5 g of 2-chloropropionyl chloride (0.05 mol) were dissolved in 100 ml of 1,4-dioxane and stirred at reflux for three hours. After evaporation of the solvent under reduced pressure, the remaining oil was purified by column chromatography. 8 g of 2-(2-chloro-1-oxopropyl)hydrazide of 4-(trifluoromethoxy)benzoic acid as a white solid was obtained. The structure was confirmed by nuclear magnetic resonance spectroscopy.

B. Preparation of 6-methyl-2-(4-trifluoromethoxy)phenyl-4H-1,3,4-oxadiazin-5(6H)-one.

8 g of the 2-(2-chloro-1-oxopropyl)hydrazide of 4-(trifluoromethoxy)benzoic acid (0.03 mol) prepared above in A was dissolved in 100 ml of acetonitrile. 3 g of triethylamine was then added and the resulting solution was stirred and refluxed for 24 hours. After cooling, the precipitate was filtered and the filtrate evaporated under reduced pressure, leaving 7.5 g of an oil. Purification by column chromatography produced 3 g of 6-methyl-2-(4-trifluoromethoxy)-phenyl-4H-1,3,4-oxadiazin-5(6H)-one as a white solid. The structure was confirmed by nuclear magnetic resonance spectroscopy.

C. Preparation of 5,6-dihydro-6-methyl-2-(4-trifluoromethoxyphenyl)-4H-1,3,4-oxadiazine.

3 g of the 6-methyl-2-(4-trifluoromethoxy)phenyl-4H-1,3,4-oxadiazin-5(6H)-one prepared above in B was dissolved in 25 ml of 1,4-dioxane. The solution was cooled to 0° C. and then 0.5 g of acetic acid was added. The reaction mixture was then refluxed for 24 hours. After cooling to room temperature, 100 ml of water was added and the mixture was extracted with 200 ml of dichloromethane. 2.6 g of an oil remained which was purified by column chromatography to produce 1.0 g of 5,6-dihydro-6-methyl-2-(4-trifluoromethoxyphenyl)-4H-1,3,4-oxadiazine as an oil. The structure was confirmed by nuclear magnetic resonance spectroscopy.

D. Preparation of 5,6-dihydro-6-methyl-2-(4-trifluoromethoxyphenyl)-N-4-trifluoromethylphenyl)-4H-1,3,4-oxadiazine-4-carboxamide.

1 g of the 5,6-dihydro-6-methyl-2-(4-trifluoromethoxyphenyl)-4H-1,3,4-oxadiazine prepared above was dissolved in 10 ml of acetonitrile. 1 g of 4-(trifluoromethyl)phenyl isocyanate was added dropwise and then the resulting reaction mixture was refluxed for two hours. Evaporation of the solvent at reduced pressure afforded 1.5 g of 5,6-dihydro-6-methyl-2-(4-trifluoromethoxy-phenyl)-N-(4-trifluoromethylphenyl)-4H-1,3,4-oxadiazine-4-carboxamide as a solid which was washed with a few milliliters of acetonitrile. The structure was confirmed by nuclear magnetic resonance spectroscopy.

Example 11

Preparation of ethyl 5, 6-dihydro-2-[4-(trifluoromethoxy)-phenyl]-N-[((4-trifluoromethylphenl)amino)carbonyl]-4H-1,3,4-oxadiazine-6-carboxylate (Compound No. 11)

A. Preparation of ethyl 5,6-dihydro-2-(4-trifluoromethoxyphenyl-4H-1,3,4-oxadiazine-6-carboxylate.

25 g of 4-(trifluoromethoxy)benzoic acid hydrazide (0.13 mol) and 30 g of ethyl 2,3-dibromopropionate (0.13 mol) were dissolved in 150 ml of acetonitrile. 26 g (0.26 mol) of triethylamine was then added and then the resultant reaction mixture was refluxed for 24 hours. After cooling, the reaction mixture was filtered and then the filtrate was evaporated under reduced pressure leaving 35 g of a crude oil. The crude oil was purified by column chromatography to afford 4.5 g of ethyl 5,6-dihydro-2-(4-trifluoromethoxyphenyl-4H-1,3,4-oxadiazine-6-carboxylate as an oil. The structure was confirmed by nuclear magnetic resonance spectroscopy.

B. Preparation of ethyl 5,6-dihydro-2-(4-trifluoromethoxyphenyl)-N-(((4-trifluoromethylphenyl)amino)-carbonyl)-4H-1,3,4-oxadiazine-6-carboxylate.

1 g of the ethyl 5,6-dihydro-2-(4-trifluoromethoxy-phenyl-4H-1,3,4-oxadiazine-6-carboxylate prepared above in A was dissolved in 15 ml of acetonitrile. 1 g of 4-(trifluoromethyl)phenyl isocyanate was added dropwise. The resulting reaction mixture was refluxed for two hours and then the solvent was evaporated under reduced pressure to produce a solid. The solid was washed with a few milliliters of acetonitrile to produce 1.2 g of ethyl 5,6-dihydro-2-(4-trifluoromethoxyphenyl)-N-(((4-trifluoromethylphenyl)amino)carbonyl)-4H-1,3,4-oxadiazine-6-carboxylate as a white solid. The structure was confirmed by nuclear magnetic resonance spectroscopy.

Example 12

Preparation of 4H-1,3,4-oxadiazine-4-carboxamide, 6-ethoxy-5,6-dihydro-N-methyl-N-[4-(trifluoromethoxy)-phenyl]-2-[3-(trifluoromethyl) phenyl]- (Compound No. 12)

1 g of 6-ethoxy-5,6-dihydro-N-[4-(trifluoromethoxy) phenyl]-2-[3-trifluoromethyl)phenyl]-4H-1,3,4-oxadiazine-4-carboxamide (Compound No. 1) was added to 0.3 g of hexane-washed sodium hydride dissolved in 20 ml of toluene and the resulting reaction mixture was heated to 60° C. for one hour. After to room temperature, 3 ml of methyl iodide was added dropwise to the reaction mixture. The reaction mixture was then stirred at room temperature for 18 hours. 100 ml of water was then added to the reaction mixture and then extracted with 100 mol of toluene. After drying over sodium sulfate, the filtered solution was evaporated under reduced pressure, to produce an oil. The oil was purified by column chromatography producing 6-ethoxy-5, 6-dihydro-N-methyl-N-[4-(trifluoromethoxy)phenyl]-2-[3-(trifluoromethyl)-phenyl]-4H-1,3,4-oxadiazine-4-carboxamide, as a viscous oil. The structure was confirmed by nuclear magnetic resonance spectroscopy.

TABLE 1

| Cmpd No. | R | $R^1$ | $R^2$ | $R^3$ | $R^4$ | $R^5$ | $R^6$ |
|---|---|---|---|---|---|---|---|
| 1 | 3-$CF_3C_6H_4$ | 4-$CF_3O$ | H | H | H | $C_2H_5O$ | H |
| 2 | 4-$BrC_6H_4$ | 4-$CF_3O$ | H | H | H | $C_2H_5O$ | H |
| 3 | 5-$BrC_4H_2S$ | 4-$CF_3O$ | H | H | H | $C_2H_5O$ | H |
| 4 | 5-$BrC_4H_2S$ | 4-$CF_3O$ | H | H | $CH_3$ | $CH_3O$ | H |
| 5 | 3-$CF_3C_6H_4$ | 4-$CF_3O$ | $CH_3$ | H | H | $C_2H_5O$ | H |
| 6[1] | 4-$BrC_6H_4$ | 4-$CF_3O$ | H | $CH_2$ | H | $CH_2O$ | H |
| 7[2] | 4-$BrC_6H_4$ | 4-$CF_3O$ | H | $CH_2CH_2$ | H | $CH_2O$ | H |
| 8 | 3-$CF_3C_6H_4$ | 4-$CF_3O$ | H | H | H | $CH_3O$ | H |
| 9 | 3-$CF_3C_6H_4$ | 4-$CF_3$ | H | H | H | $C_2H_5O$ | H |
| 10 | 4-$CF_3O$—$C_6H_4$ | 4-$CF_3$ | H | H | H | $CH_3$ | H |
| 11 | 4-$CF_3O$—$C_6H_4$ | 4-$CF_3$ | H | H | H | $C_2H_5OC(O)$— | H |
| 12 | 3-$CF_3C_6H_4$ | 4-$CF_3O$ | H | H | H | $C_2H_5O$ | $CH_3$ |
| 13 | 3-$CF_3C_6H_4$ | 4-$CF_3O$ | H | H | H | $C_2H_5O$ | $(CH_3)_3C$-O-C(O)— |

[1]$R^3$ and $R^5$ together form a 5-membered ring (furan)
[2]$R^3$ and $R^5$ together form a 6-membered ring (pyran)

TABLE 2

NMR DATA

| Compound No. | NMR Data (ppm) in DMSO |
|---|---|
| 1 | t (3) 1.2; m (4) 3.5–4.1; t (1) 5.7; m (8) 7.0–7.9; s (1) 9.4 |
| 2 | t (3) 1.2; m (4) 3.5–4.1; t (1) 5.4; m (8) 7.0–8.5; s (1) 8.4 |
| 3 | t (3) 1.2; m (4) 3.5–4.1; t (1) 5.4; m (8) 7.0–7.8; s (1) 8.3 |
| 4 | s (3) 1.5; d (1) 3.2; s (3) 3.4; q (1) 4.3; m (6) 6.9–7.8; s (1) 8.3 |
| 5 | t (3) 1.1; t (3) 1.3; q (2) 3.8; m (1) 4.4–4.8; d (1) 5.6; m (8) 7.1–8.2; s (1) 9.4 |
| 6 | m (2) 1.4–2.0; m (2) 3.5–3.9; m (1) 4.4–4.7; d (1) 5.7; m (8) 7.1–8.2; s (1) 9.4 |
| 7 | m (4) 1.4–2.2; m (2) 3.9–4.4; m (1) 4.8–5.2; d (1) 5.7; m (8) 7.1–8.2; s (1) 9.4 |
| 8 | s (3) 3.6; m (2) 3.3–4.3; t (1) 5.7; m (8) 7.1–8.6; s (1) 9.4 |
| 9 | t (3) 1.2; m (4) 3.5–4.3; t (1) 5.9; m (8) 7.5–8.6; s (1) 9.6 |
| 10 | d (3) 1.5; m (1) 3.3–3.6; m (2) 4.3–4.8; m (8) 7.5–8.3; s (1) 9.5 |
| 11 | t (3) 1.2; m (4) 3.9–4.6; t (1) 5.7; m (8) 7.4–8.3; s (1) 9.5 |
| 12 | t (3) 1.2; s (3) 3.3; m (4) 3.9–4.6; t (1) 5.7; m (8) 7.4–8.3 |

Example A

Stock Solution Preparation

The remaining examples relate to the insecticidal use of the compounds of this invention. In all these examples, a stock solution for the compounds was prepared at 1000 ppm by dissolving 0.13 gram of each compound to be tested in 13 ml of acetone and adding 117 ml of distilled water plus 5 drops of ethoxylated sorbitan monolaurate, a wetting agent. This stock solution was used in the remaining examples demonstrating the insecticidal use of representative compounds of this invention. For each example that follows, this stock solution was used and the specificized dilutions made. All the tests discussed below, which involved treatment with compounds of this invention were always repeated with controls, in which the active compound was not provided, to permit a comparison upon which the percent control was calculated.

Example B

Southern Corn Rootworm Test

The stock solution of 1000 ppm prepared in Example A above, was diluted to 100 ppm (test solution). For each compound, 2.5 ml of the test solution was pipetted onto a filter paper (Whatman #3) at the bottom of a 100 mm petri dish. Two corn seedlings were soaked in the 100 ppm solution for 1 hour and transferred to the petri dish containing the same test solution. After 24 hours, each dish was loaded with 5 second instar larvae of Southern Corn Rootworm (*Diabrotica undecimpunctata*). After five days, the number of live larvae was noted and the percent control, corrected by Abbott's formula [see J. Economic Entomology 18: 265–267 (1925)] was calculated.

The results of the testing of Southern Corn Rootworm (CR) are presented in Table 3 below.

Example C

Rice Planthopper Foliar Test

The stock solution of 1000 ppm prepared in Example A above, was used undiluted. One pot containing approximately 20 Mars variety rice seedlings was treated with each formulation by spraying with a spray atomizer. One day after treatment plants were covered with a tubular cage and twenty adult rice delphacids, *Sogatodes orizicola*, were transferred into each cage. Five days after transferring, counts were made of the surviving planthoppers in each pot and percent control was estimated.

Results of the testing of rice planthoppers (RPH) are presented in Table 3 below.

Example D

Tobacco Budworm Test

For each compound, 0.2 ml of the stock solution prepared in Example A above, was pipetted onto the surface of each of 5 diet cells, allowed to spread over the surfaces and air dried for two hours. Then a second instar *Helicoverpa virescens* larva was introduced into each cell. After 14 days, the number of living larvae was determined for each treatment and percent control, corrected by Abbott's formula, was calculated.

The results of the testing of tobacco budworms (TB) are presented in Table 3 below.

TABLE 3

PERCENT CONTROL OF SOUTHERN CORN ROOTWORM, RICE PLANTHOPPER AND TOBACCO BUDWORM

| Compound No. | Percent Control | | |
|---|---|---|---|
| | CR | RPH | TB |
| 1 | 100 | 0 | 100 |
| 2 | 0 | 0 | 100 |
| 3 | 80 | 0 | 100 |
| 4 | 80 | 0 | 100 |
| 5 | 100 | 0 | 100 |
| 6 | 0 | 0 | 100 |
| 7 | 100 | 100 | 52 |
| 8 | 100 | 0 | 100 |
| 9 | 100 | 0 | 100 |
| 10 | 0 | 0 | 100 |
| 11 | 0 | 0 | 37 |
| 12 | 40 | 100 | 100 |

What is claimed is:

1. A compound having the formula:

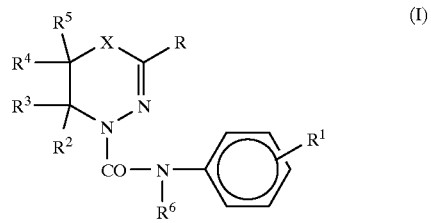

wherein X is O, N or S; R is phenyl, a $C_4$–$C_5$ heterocyclic group containing one nitrogen, sulfur, or oxygen atom, wherein the phenyl or heterocyclic group is unsubstituted or mono-, di-, or tri-substituted with halogen, $C_1$–$C_4$ haloalkyl, or $C_1$–$C_4$ haloalkoxy; $R^1$ is halogen, $C_1$–$C_4$ haloalkyl or $C_1$–$C_4$ haloalkoxy; $R^2$, $R^3$, and $R^4$ are, independently, hydrogen, $C_1$–$C_6$ alkyl or $C_1$–$C_6$ alkoxy; $R^5$ is nitro, cyano, $C_1$–$C_6$ alkyl, di($C_1$–$C_6$)alkylamino, $C_1$–$C_6$ alkylthio, $C_1$–$C_6$ alkoxy, $C_1$–$C_6$ haloalkoxy, phenoxy, phenylthio, or ($C_1$–$C_6$ alkoxy)carbonyl; $R^6$ is hydrogen, $C_1$–$C_6$ alkyl, $C_1$–$C_4$ alkylthio, ($C_1$–$C_4$ alkoxy)$C_1$–$C_4$ alkyl, $C_2$–$C_8$ acyl, or benzyl, wherein $R^3$ and $R^5$ together can form a ring.

2. A compound as recited in claim 1 having the formula:

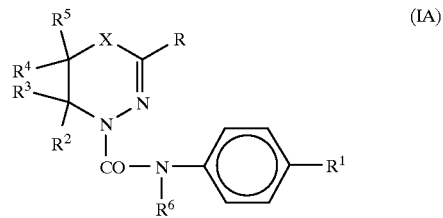

wherein R, $R^1$, $R^2$, $R^3$, $R^4$, $R^5$, $R^6$, and X are as described in claim 1.

3. A compound as recited in claim 2 wherein R is phenyl, thienyl, furanyl, or pyridinyl, optionally mono-, di- or tri-substituted by bromo, chloro, $C_1$–$C_4$ alkyl, $C_1$–$C_4$ trihaloalkyl, or $C_1$–$C_4$ trihaloalkoxy.

4. A compound as recited in claim 3 wherein X is O; $R^1$ is $C_1$–$C_4$ trihaloalkyl or $C_1$–$C_4$ trihaloalkoxy; $R^2$, $R^3$, and $R^4$ are, independently, $C_1$–$C_4$ alkyl or $C_1$–$C_4$ alkoxy; $R^5$ is $C_1-C_4$ alkoxy, $C_1-C_4$ alkyl, $C_1-C_4$ alkylthio, or di($C_1-C_4$) alkylamino; and $R^6$ is hydrogen, $C_1-C_4$ alkyl, $C_1-C_4$ alkylthio, ($C_1-C_4$ alkoxy)methyl, or $C_2-C_8$ acyl.

5. A compound as recited in claim 4 wherein R is phenyl, thienyl, furanyl, or pyridinyl, optionally mono-substituted by one bromo, one chloro, one methyl, one t-butyl, one trihalomethyl, one trihaloethyl, one trihalomethoxy, or one trihaloethoxy.

6. A compound as recited in claim 5 wherein $R^1$ is trihalomethyl or trihaloethyl; $R^2$, $R^3$, and $R^4$ are, independently, methyl, ethyl, methoxy, or ethoxy; $R^5$ is methoxy or ethoxy; and $R^6$ is methyl, methylthio, methoxymethyl or acetyl.

7. A compound as recited in claim 6 wherein R is phenyl, thienyl, pyridinyl, or benzothienyl, substituted by bromo, chloro, methyl, t-butyl, trifluoromethyl, or trifluoromethoxy.

8. An insecticidal composition comprising: a) an effective amount of a compound as recited in claim 1; and b) a suitable carrier.

9. An insecticidal composition comprising: a) an effective amount of a compound as recited in claim 2; and b) a suitable carrier.

10. An insecticidal composition comprising: a) an effective amount of a compound as recited in claim 4; and b) a suitable carrier.

11. An insecticidal composition comprising: a) an effective amount of a compound as recited in claim 5; and b) a suitable carrier.

12. A method for controlling insects which comprises applying an effective amount of a compound as recited in claim 1 to the locus to be protected.

13. A method for controlling insects which comprises applying an effective amount of a compound as recited in claim 2 to the locus to be protected.

14. A method for controlling insects which comprises applying an effective amount of a compound as recited in claim 4 to the locus to be protected.

15. A method for controlling insects which comprises applying an effective amount of a compound as recited in claim 5 to the locus to be protected.

* * * * *